(12) United States Patent
Woo et al.

(10) Patent No.: US 7,417,161 B2
(45) Date of Patent: Aug. 26, 2008

(54) CONTINUOUS METHOD FOR PREPARING AROMATIC CARBONATE USING A HETEROGENEOUS CATALYST AND A REACTION APPARATUS FOR THE SAME

(75) Inventors: Boo-Gon Woo, Daejeon (KR); Ja-Hun Kwak, Daejeon (KR); Moo-Ho Hong, Daejeon (KR); Mi-Jeung Hong, Jeollanam-do (KR)

(73) Assignee: LG Chem. Ltd. (KR)

( * ) Notice: Subject to any disclaimer, the term of this patent is extended or adjusted under 35 U.S.C. 154(b) by 295 days.

(21) Appl. No.: 10/502,435

(22) PCT Filed: Feb. 3, 2003

(86) PCT No.: PCT/KR03/00237

§ 371 (c)(1),
(2), (4) Date: Jun. 9, 2005

(87) PCT Pub. No.: WO03/066569

PCT Pub. Date: Aug. 14, 2003

(65) Prior Publication Data

US 2005/0240046 A1     Oct. 27, 2005

(30) Foreign Application Priority Data

Feb. 5, 2002   (KR) ................. 10-2002-0006585
Jan. 15, 2003  (KR) ................. 10-2003-0002772

(51) Int. Cl.
*C07C 69/96* (2006.01)
(52) U.S. Cl. ...................................... 558/270; 558/274
(58) Field of Classification Search ............. 558/270, 558/274
See application file for complete search history.

(56) References Cited

U.S. PATENT DOCUMENTS

| | | | |
|---|---|---|---|
| 4,045,464 A | 8/1977 | Romano et al. | 260/463 |
| 4,182,726 A | 1/1980 | Illuminati et al. | 260/463 |
| 4,552,704 A | 11/1985 | Mark | 260/463 |
| 4,554,110 A | 11/1985 | Mark | 260/463 |
| 4,609,501 A | 9/1986 | Mark | 260/463 |
| 5,034,557 A | 7/1991 | Kiso et al. | 558/270 |
| 5,210,268 A | 5/1993 | Fukuoka et al. | 558/270 |
| 5,354,923 A | 10/1994 | Schon et al. | 558/270 |
| 5,380,908 A | 1/1995 | Murata et al. | 558/270 |
| 5,426,207 A | 6/1995 | Harrison et al. | 558/274 |
| 5,523,451 A | 6/1996 | Rechner et al. | 558/270 |
| 5,565,605 A | 10/1996 | Tsuneki et al. | 560/109 |
| 5,872,275 A * | 2/1999 | Komiya et al. | 558/270 |
| 5,922,826 A | 7/1999 | Kuze et al. | |
| 6,057,470 A | 5/2000 | Tsuneki et al. | 558/270 |

FOREIGN PATENT DOCUMENTS

| | | |
|---|---|---|
| CN | 1123270 A | 5/1996 |
| EP | 0 855 384 A1 | 7/1998 |
| JP | 4-224547 | 8/1992 |
| JP | 4-266856 | 9/1992 |
| JP | 8269185 | 10/1996 |
| JP | 2000128977 | 5/2000 |

OTHER PUBLICATIONS

PCT International Search Report; International application No. PCT/KR03/00237; International filing date: Feb. 3, 2003; Date of Mailing: Apr. 18, 2003.
PCT International Preliminary Examination Report; International application No. PCT/KR2003/000237; International filing date: Feb. 3, 2003; Date of Completion: Jun. 2, 2004.

\* cited by examiner

*Primary Examiner*—Rei-Tsang Shiao
(74) *Attorney, Agent, or Firm*—Lerner, David, Littenberg, Krumholz & Mentlik, LLP

(57) ABSTRACT

The present invention relates to a continuous method for the preparation of an aromatic carbonate by reacting a dialkyl carbonate and an aromatic hydroxy compound in the presence of a heterogeneous catalyst, and a reaction apparatus for the same. The continuous method comprises the step of reacting dialkyl carbonate and an aromatic hydroxy compound in the presence of the heterogeneous catalyst in a loop-type, catalyst-containing reaction apparatus, wherein a reactor equipped with a filter in which the catalyst is contained is connected with a heat exchanger portion for providing necessary heat during the reaction, reaction solution is circulated between the catalyst-containing portion and heat exchanger via a circulation pump, and by-products can be eliminated via a distillation column connected with the reactor.

5 Claims, 1 Drawing Sheet

CONTINUOUS METHOD FOR PREPARING AROMATIC CARBONATE USING A HETEROGENEOUS CATALYST AND A REACTION APPARATUS FOR THE SAME

This application is a 371 of PCT/KR03/00237 filed on Feb. 3, 2003.

BACKGROUND OF THE INVENTION (a) Field of the Invention

The present invention relates to a method for preparing an aromatic carbonate and a reaction apparatus for the same, and particularly to a continuous method for preparing an aromatic carbonate using a heterogeneous catalyst and a reaction apparatus for the same.

(b) Description of the Related Art

Aromatic carbonates are used as starting materials in the preparation of several kinds of isocyanates and aromatic polycarbonates that do not use a very toxic phosgene gas, and they are synthesized mostly by the transesterfication of dialkyl carbonates and aromatic hydroxy compounds. In this reaction, typical reactants are dimethyl carbonate and phenol.

However, such transesterfication is a reversible reaction and its equilibrium constant is very small, and consequently the conversion rate after reaction is very low and the reaction rate is quite slow, and thus it has numerous difficulties in being used in commercial production.

Several attempts have been made to solve such problems, including attempting to increase the reaction rate by improving the performance of a reaction catalyst.

U.S. Pat. No. 4,182,726 disclosed a process of using an $AlX_3$ such as $AlCl_3$, $UX_3$, $TiX_3$, $VOX_3$, $VX_3$, $ZnX_2$, $FeX_3$, and $SnX_3$ class reaction catalysts, wherein X refers to halogen group elements. Also, U.S. Pat. No. 4,045,464 disclosed using Ti class compounds such as titanium tetraphenate or Lewis acids.

Further, U.S. Pat. No. 4,552,704 disclosed Ti and Sn class reaction catalysts such as butyltin oxide hydroxide, U.S. Pat. No. 4,554,110 disclosed polymeric tin compounds as reaction catalysts, and U.S. Pat. No. 4,609,501 disclosed a reaction catalyst mixing at least one Lewis acid and at least one protic acid.

These prior arts can be said to try to improve the reaction rate by the action of the reaction catalyst rather than to improve reactivity by the reaction process, in order to increase efficiency in the preparation of DPC (diphenyl carbonate) from DMC (dimethyl carbonate).

However, all of the catalysts proposed in these patents are homogeneous catalysts, and thus when they are used they should be mixed with reactants in a certain ratio. Also, even though reaction by-products such as methanol, which are generated during reaction, were allowed to be continuously eliminated from the reaction system, the reaction rates shown in the examples were not high.

On the other hand, there have been attempts to use heterogeneous catalysts as reaction catalysts. U.S. Pat. No. 5,354,923 employed a stirring reactor using a catalyst in a powdered form having a surface area of not less than 20 $m^2/g$, and U.S. Pat. No. 5,565,605 applied heterogeneous catalysts such as titanoalumino phosphate for reaction.

However, the heterogeneous catalysts prepared hitherto are in a powdered form and they are subject to reaction and separation processes together with the reactants, and thus they cause a problem of being adhered to the inside walls of pipes and equipment. They are also problematic in their reuse after separation because they co-exist with reaction products having a high boiling point.

Further, there have been attempts to increase efficiency in the preparation of DPC by designing unique reaction processes along with the development of reaction catalysts. U.S. Pat. No. 5,210,268 employed a multi-stage distillation column as a reactor, wherein two reactants having different boiling points were counter-currently contacted by injecting the reactant having a high boiling point to the upper portion of the column together with a homogeneous catalyst and by heating and evaporating the reactant having a low boiling point at the bottom portion of the column to synthesize an aromatic carbonate.

Also, U.S. Pat. No. 5,426,207 disclosed a reaction process using three reactors that were connected in series, and U.S. Pat. No. 5,523,451 disclosed a process of applying multiple bubble columns that were connected in series to a reactor. Also, U.S. Pat. No. 6,057,470 disclosed a reaction process using a reaction distillation method.

However, these processes have numerous difficulties in the separation of catalysts because they use homogeneous catalysts or catalysts in a powdered form, and they also have difficulties in economic aspects because a certain amount of catalyst must be continuously supplied to the reaction system in a continuous operation.

SUMMARY OF THE INVENTION

The present invention has been made in consideration of the problems of the prior arts as described above, and it is an object of the invention to provide a continuous method for preparing an aromatic carbonate that can solve all of the problems as mentioned above, is suitable for commercial production, and can be operated at a low cost, and a reaction apparatus for the same.

It is another object of the invention to provide a continuous method for preparing an aromatic carbonate by reacting a dialkyl carbonate and an aromatic hydroxy compound in the presence of a heterogeneous catalyst, wherein the catalyst and reactants do not adhere to the inside walls of pipes and equipment because they are not subjected to reaction and separation processes, and the reaction products having a high boiling point and the catalyst do not co-exist, and a reaction apparatus for the same.

It is a further object of the invention to provide a continuous method for preparing an aromatic carbonate with a low cost and that is capable of minimizing catalyst separation processes and costs that might exist in the homogeneous catalyst-based processes requiring the continuous injection of new catalyst to the reactor, by reacting a dialkyl carbonate and an aromatic hydroxy compound using a heterogeneous catalyst, and a reaction apparatus for the same.

In order to achieve aforementioned objects, the present invention provides a continuous method for preparing an aromatic carbonate comprising the step of reacting a dialkyl carbonate and an aromatic hydroxy compound in the presence of a heterogeneous catalyst in a loop-type, catalyst-containing reaction apparatus.

Also, the invention provides a reaction apparatus for the continuous preparation of an aromatic carbonate, comprising a) a reactor equipped with a filter, which is located inside the reactor, for preventing the output of a heterogeneous catalyst and only outputting reaction solution;

b) a reaction solution circulation pump that is connected to the side of the reactor on which the filter is equipped;

c) a heat exchanger, which is connected between the reaction solution circulation pump and the reactor, for raising the temperature of the reaction solution that is supplied from the reaction solution circulation pump to a desired reaction temperature and evaporating it; and d) a distillation column, which is connected to the upper portion of the reactor, for separating the evaporated reactants that are generated in the reactor and the heat exchanger into high boiling point components and low boiling point components and then condensing the high boiling point components to withdraw and direct them to the reactor and outputting the low boiling point components in a gaseous form.

Furthermore, the reaction apparatus may further comprise e) a heat exchanger for cooling, which is connected to the upper portion of the distillation column, for condensing the low boiling point components that are supplied from the distillation column in a gaseous form.

Figure 1:
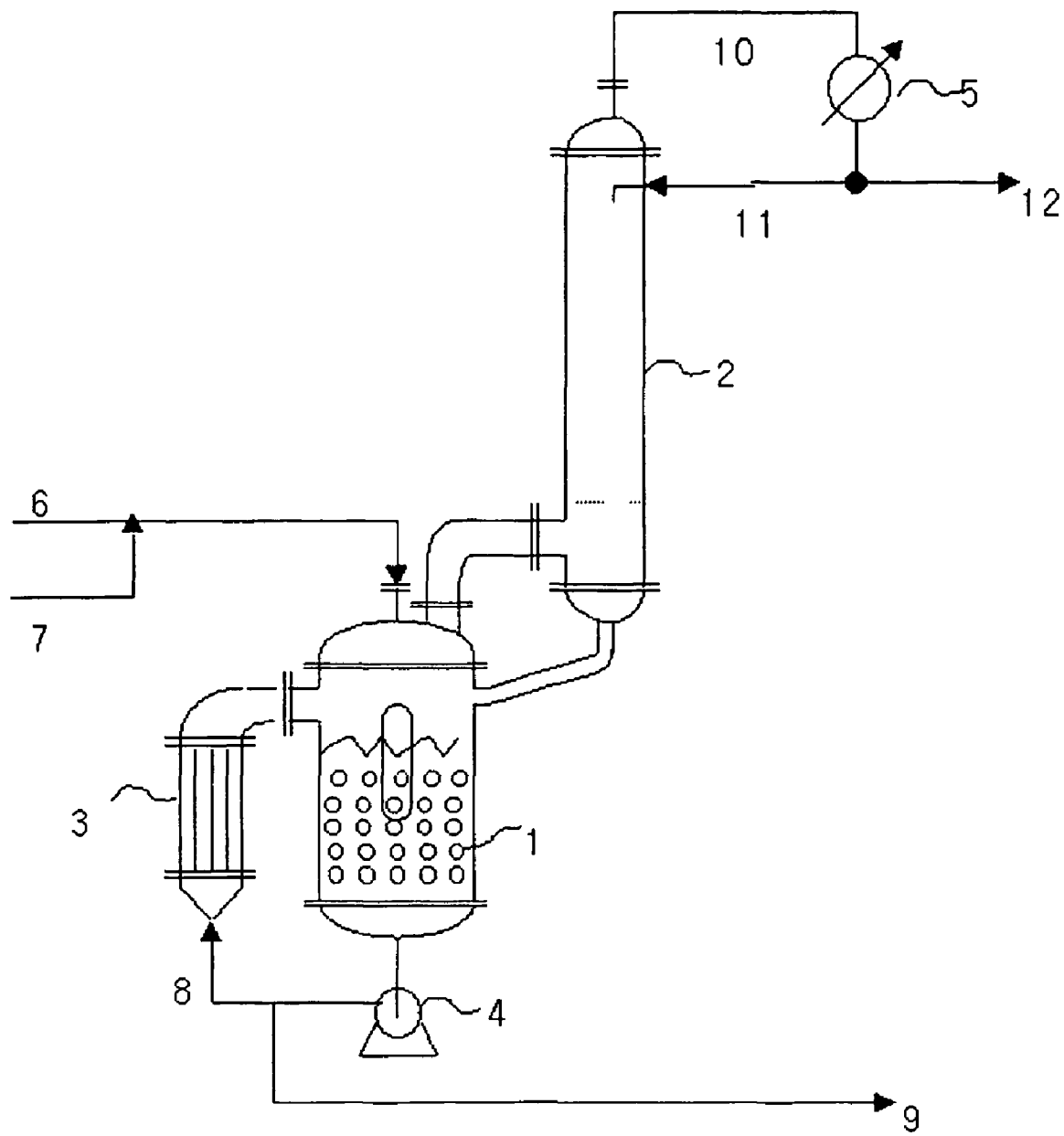
FIG. 1 is a schematic view showing the loop-type reaction apparatus of the present invention.

Reference numeral 1 is a reactor equipped with a filter, 2 is a distillation column, 3 is a heat exchanger for heating, 4 is a reaction solution circulation pump, 5 is a heat exchanger for cooling, and 6, 7, 8, 9, 10, 11, and 12 are pipes.

DETAILED DESCRIPTION OF THE PREFERRED EMBODIMENTS

The present invention will be hereafter described in detail.

The present invention relates to a continuous method for preparing an aromatic carbonate using a heterogeneous catalyst and using a dialkyl carbonate and an aromatic hydroxy compound such as phenol as starting materials to prepare an aromatic carbonate and a mixture thereof, and a reaction apparatus for the same, characterized in that in order to eliminate reaction by-products generated during the reaction, a loop-type circulation reactor equipped with a distillation column and silica-supported heterogeneous catalysts are used.

The aromatic carbonate prepared by the present invention is used as a starting material in the preparation of several kinds of isocyanates and aromatic polycarbonates that do not use a very toxic phosgene gas, and it is synthesized by the transesterfication of a dialkyl carbonate and an aromatic hydroxy compound. This transesterfication is an equilibrium reaction that can achieve high reactivity by continuously eliminating by-products with a relatively low boiling point that are generated by the reaction. The reaction system provided in the present invention is a reactor system suitable for continuous elimination of the reaction by-products as described above, and its efficacy was verified by actual reaction experiments that showed reactivity characteristics such as conversion rate, selectivity, etc. to be high. Also, the reactor system of the present invention is an economical reaction system that lowers costs and minimizes catalyst separation processes that might exist in the homogeneous catalyst-based processes requiring the continuous injection of new catalyst to the reactor, by using a heterogeneous catalyst as a reaction catalyst.

For these purposes, the present invention uses a catalyst that is prepared by supporting various kinds of transition metal oxides on silica so as to solve the problems of separation and re-charging of a reaction catalyst, and it provides a uniquely designed loop-type, catalyst-containing reaction apparatus so as to maximize the supported catalyst. The aromatic carbonate can be efficiently prepared from such a reaction apparatus.

The present invention is directed to a process for preparing an aromatic carbonate from dialkyl carbonates, wherein the dialkyl carbonate can be represented by the following Chemical Formula 1:

Chemical Formula 1

ROCOR

In the above Chemical Formula 1, R is an alkyl group. The alkyl group as used herein refers to a general alkyl group such as methyl, ethyl, propyl, butyl, and cyclohexyl groups.

The dialkyl carbonate is transesterified with an aromatic hydroxy compound represented by ArOH (Ar is an aromatic group) to synthesize an alkyl aryl carbonate represented by Chemical Formula 2 or Chemical Formula 3 as shown below, and an alkyl alcohol is generated as a reaction by-product.

Chemical Formula 2

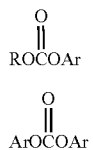

ROCOAr

Chemical Formula 3

ArOCOAr

In the above Chemical Formula 2 and 3, each Ar is an aromatic group having 5 to 30 carbon atoms.

A typical reaction formula relating to the reaction process designed in the invention can be represented by the following Reaction Formulae 1 to 3:

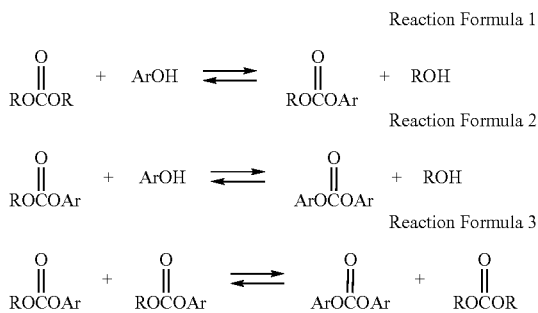

In the above reaction Formula 1, 2, and 3, R is an alkyl group and Ar is an aromatic group.

The reactions shown in the above are reversible reactions having a reaction equilibrium, they can obtain a high reaction conversion rate by extracting the reaction by-products that are generated during the reaction to the outside of the reaction system, and they can increase the reaction rate by using efficient reaction catalysts.

In the prior preparation of aromatic carbonates, stirring reactors, which mostly use homogeneous catalysts, were used and by-products having a low boiling point, which are generated during the reaction, were eliminated using the distillation column installed in the reactors. However, process difficulties have been encountered in the use of homogeneous catalysts because the catalytic components adhere to the inside walls of pipes and equipment used in the process, the catalysts used must be separated and eliminated, and the catalysts must be continuously supplied to the reactor in continuous reaction so it is costly.

As a different method, instead of the stirring reactors, there has been an attempt to increase reactivity by installing several reaction distillation columns capable of performing reaction and separation of by-products at the same time, but as it used homogeneous or heterogeneous catalysts in a powdered form, problems generated by the catalysts still exist.

In order to solve the problems generated by the reaction catalysts of the prior arts, the present invention preferably uses a catalyst where one or more transition metal oxides selected from, for example, $MoO_3$, $Ga_2O_3$, $V_2O_5$, PbO, $ZrO_2$, $TiO_2$, CdO, $Fe_2O_3$, CuO, MgO, $Y_2O_3$, $Mn_3NiO$, ZnO, $Nd_2O_3$, $Co_2O_3$, $RuO_2$, $Nb_2O_5$, and $Cr_2O_3$ are supported on a carrier such as silica having a size of 1 to 20 mm and having the shape of a sphere, cylinder, ring, etc., as a heterogeneous catalyst. The specific surface area of the silica is 20 to 500 $m^2/g$ and more preferably 100 to 300 $m^2/g$, and the porosity is 0.25 to 0.8 $cm^2/g$ and more preferably 0.4 to 0.75 $cm^2/g$.

However, the silica-supported heterogeneous catalyst as described above has a problem of a low reaction activity in comparison with the volume or weight of the catalyst. Hence, the invention uses a loop-type, specific reaction apparatus so as to solve such problem. An embodiment of this reaction apparatus is illustrated in FIG. 1.

The loop-type, catalyst-containing reaction apparatus used in the invention is very suitable in the preparation of aromatic carbonates using heterogeneous catalysts having a size of approximately 1 to 20 mm, and it is a loop-type reaction apparatus wherein a reactor equipped with a filter in which the catalyst is contained is connected with a heat exchanger portion for providing necessary heat during reaction. The reaction solution is circulated during the reaction between the catalyst-containing portion and the heat exchanger by a circulation pump, and by-products can be eliminated through a distillation column connected to the reactor.

More particularly, the loop-type, catalyst-containing reaction apparatus of the present invention comprises a reactor in which the catalyst is contained. Inside of reactor 1, preferably at the bottom portion, is a filter (not shown in the drawing) that does not output the heterogeneous catalyst but rather it readily outputs the reaction solution only, and a certain amount of the supported heterogeneous catalyst is charged into the reactor, through the upper portion of the filter. The amount of the catalyst to be charged is determined by the amount of the aromatic carbonate to be produced. That is to say, after the amount of the aromatic carbonate prepared during a given time by a certain amount of the catalyst is experimentally determined, the amount of the heterogeneous catalyst necessary for the production can be determined.

After a certain amount of catalyst is charged, a calculated amount of dialkyl carbonate or alkyl aryl carbonate, and an aromatic hydroxy compound, are continuously injected into the reactor separately or in the form of a mixture via pipe 6 and pipe 7, which are able to continuously supply feeds. If the amount of reaction solution in reactor 1 is above a certain amount, the reaction solution is circulated between reactor 1 and heat exchanger 3 via pipe 8 using circulation pump 4. A portion of the reaction solution circulated is output to the outside of the reaction system via pipe 9 by the control of the level of the reactor. During the circulation of the reaction solution, the temperature is raised to a desired reaction temperature using heat exchanger 3, which provides evaporation heat to components having a comparatively low boiling point such as alkyl alcohol, which is a reaction by-product, thus enabling the reaction by-products to be readily extracted.

The low boiling point components and the reaction by-products evaporated by heat exchanger 3 are input into distillation column 2, where active components having a relatively high boiling point are condensed and drawn into reactor 1.

The alkyl alcohol, which is the reaction by-product, and alkyl carbonates having a relatively low boiling point, are not condensed and they are input into the heat exchanger 5 via pipe 10 in a gaseous form and condensed by cooling, and then all or part of the condensate is refluxed into distillation column 2 via pipe 11 or all or a part is disposed of via pipe 12.

In the continuous preparation method of the present invention, the high boiling point components comprising a desired aromatic carbonate (final reactant) are disposed of via pipe 9 or they may be disposed of directly from the side of reactor 1 on which the filter is equipped, and the disposed aromatic carbonate reactants are subjected to conventional purification processes such as distillation or crystallization. When the aromatic carbonate is synthesized using the continuous preparation method of the invention, operation of the process is very easy and the activity of the catalyst is maintained for a long time.

The present invention will be described with reference to the following examples in more detail. However, the examples are provided solely to illustrate the present invention, and the present invention should not be limited thereto.

EXAMPLES

Numbers shown in the following examples are calculated according to the following calculation formula:

$$\text{Conversion Rate of Phenol} = \frac{\text{Mole of the } MPC \text{ Produced} + \text{Mole of the } DPC \text{ Produced} \times 2}{\text{Mole of the Phenol Charged}}$$ [Calculation Formula 1]

$$\text{Yield of } MPC \text{ (wt. \%)} = \frac{\text{Weight of the } MPC \text{ Produced}}{\text{Weight of the Phenol Charged}}$$ [Calculation Formula 2]

$$\text{Yield of } DPC \text{ (wt. \%)} = \frac{\text{Weight of the } DPC \text{ Produced}}{\text{Weight of the Phenol Charged}}$$ [Calculation Formula 3]

$$\text{Productivity of Catalyst} = \frac{\text{Production Amount of } MPC \text{ (or } DPC\text{) per Hour (g/hr)}}{\text{Weight of Catalyst in Reactor (kg)}}$$ [Calculation Formula 4]

Example 1

Dimethyl carbonate (DMC) was used as a source of dialkyl carbonate, and as an aromatic hydroxy compound, phenol was used. Dimethyl carbonate (DMC) and phenol, which are starting materials, were pre-mixed at a molar ratio of 3:1 and then they were continuously injected into the reactor using a quantitative high pump at a flow rate of 33.3 g/minute.

The reaction temperature was 160° C., the reaction pressure was maintained at 4 atmospheres, and the flow rate of the reaction solution circulated by the circulation pump was maintained at 6.0 L/minute. The reaction was continuously carried out under the same conditions for 12 hours or longer. The catalyst used was a heterogeneous catalyst of titania ($TiO_2$) supported on silica having a diameter of 3 mm, and the amount of the catalyst contained in the reactor was 1200 g.

As a result of the reaction, the yield of methyl phenyl carbonate (MPC) was 21.7 wt. %, and the yield of dimethyl carbonate (DPC) was 0.34 wt. %. The productivity of the catalyst used was 92.6 MPC(g)/catalyst(kg)·hr.

Examples 2~7

The same continuous reaction as used in Example 1 above was carried out, except that the reaction conditions were changed as shown in Table 1 below. The reaction results are also shown in Table 1.

TABLE 1

| | Category | Ex. 2 | Ex. 3 | Ex. 4 | Ex. 5 | Ex. 6 | Ex. 7 |
|---|---|---|---|---|---|---|---|
| Reaction Condition | Temperature (° C.) | 160 | 170 | 160 | 170 | 160 | 180 |
| | Pressure (kg) | 4 | 5 | 4.5 | 5.5 | 4.5 | 4.5 |
| | Molar Ratio | 3 | 3 | 5 | 5 | 5 | 5 |
| | Feed Rate (g/min) | 11.5 | 11.5 | 11.5 | 11.5 | 22.4 | 33.3 |
| Reaction Result | Molar Conversion Rate of Phenol (%) | 18.46 | 20.59 | 24.95 | 26.64 | 18.82 | 11.79 |
| | Yield of MPC (wt. %) | 21.08 | 32.29 | 39.30 | 41.98 | 29.65 | 18.55 |
| | Yield of DPC (wt. %) | 0.54 | 0.69 | 0.72 | 0.75 | 0.54 | 0.36 |
| | Total Feed Amount (g/h) | 690 | 690 | 690 | 690 | 1344 | 1998 |
| | Feed Amount of Phenol (g/h) | 178.2 | 178.2 | 119.3 | 119.3 | 232.3 | 345.3 |
| | Yield of MPC (g/h) | 53.2 | 59.3 | 48.1 | 51.3 | 70.6 | 65.8 |
| | Productivity of Catalyst (MPC g/catalyst kg · h) | 44.3 | 49.4 | 40.1 | 42.8 | 58.9 | 54.8 |

Example 8

In order to synthesize diphenyl carbonate (DPC) using the reaction system shown in FIG. 1, a considerable amount of dimethyl carbonate (DMC) was eliminated from the reaction products prepared from Examples 1 to 7 above using a distillation apparatus, and 50 liters of reactants were obtained with a certain compositional ratio. The compositional ratio of the reactants was an insignificant amount of methanol, 34.44 wt. % of dimethyl carbonate (DMC), 13.92 wt. % of methylphenyl carbonate, 51.64 wt. % of phenol, and 0.01 wt. % of diphenyl carbonate (DPC).

The catalyst used in the synthesis of the diphenyl carbonate was a heterogeneous catalyst where titania (TiO$_2$) was supported on silica having a diameter of 3 mm, and the amount of the catalyst contained in mounted on the reactor was 1200 g. The reactants having the above-mentioned compositional ratio were continuously injected into the reactor, which is designed in the invention, at a constant flow rate of 1592 g/hr using a quantitative pump. The reaction temperature was maintained at 173° C. and the reaction pressure was maintained at 550 mbar.

During the continuous reaction, the reaction by-products having a compositional ratio of 0.2 wt. % of methanol, 43.59 wt. % of dimethyl carbonate (DMC), 2.68 wt. % of methylphenyl carbonate (MPC), 53.52 wt. % of phenol, and an insignificant amount of diphenyl carbonate (DPC) and unreacted reactants were discharged at a constant flow rate of 1274 g/hr via pipe 12, which is located in the upper portion of the reactor. The reaction products comprising a large quantity of diphenyl carbonate (DPC) were prepared at a constant flow rate of 318 g/hr via pipe 9 which is located at the bottom of the reactor.

The compositional ratio of the reaction products thus prepared was 1.49 wt. % of DMC, 26.52 wt. % of MPC, 30.90 wt. % of phenol and 41.09 wt. % of DPC. The productivity of the catalyst in this reaction was 111 DPC g/catalyst kg·hr.

Example 9

The same reaction system as in Example 1 was used, and reactants having the same compositional ratio were continuously injected into the reactor and reacted. In this example, the flow rate of the reactants to be injected was increased to 2750 g/hr to improve the productivity of the catalyst.

The reaction temperature was maintained at 165° C., and the reaction pressure was maintained at 550 mbar. During the continuous reaction, the reaction by-products having a compositional ratio of 0.23 wt. % of methanol, 47.95 wt. % of dimethyl carbonate (DMC), 1.09 wt. % of methylphenyl carbonate (MPC), 50.73 wt. % of phenol, and an insignificant amount of diphenyl carbonate (DPC) and unreacted reactants were discharged at a constant flow rate of 2094 g/hr via pipe 12, which is located in the upper portion of the reactor, and the reaction products comprising a large quantity of diphenyl carbonate (DPC) were prepared at a constant flow rate of 656 g/hr via pipe 9 which is located at the bottom of the reactor.

The compositional ratio of the reaction products thus prepared was 2.74 wt. % of DMC, 28.65 wt. % of MPC, 40.57 wt. % of phenol, and 28.04 wt. % of DPC. The productivity of the catalyst in this reaction was 142 DPC g/catalyst kg.hr.

The preparation method and the reaction apparatus for the same in the invention enable an aromatic carbonate to be continuously prepared with a low cost by reacting a dialkyl carbonate and an aromatic hydroxy compound in the presence of a heterogeneous catalyst, wherein the catalyst and reactants do not cause a problem of being adhered to the inside walls of pipes and equipment because they are not subjected to reaction and separation processes, and reaction products having a high boiling point and the catalyst do not co-exist.

What is claimed is:

1. A continuous method for the preparation of an aromatic carbonate compound, of

formula (2)

or

 formula (3)

comprising the steps of:
provide a heterogeneous catalyst on a carrier in a loop-type reaction apparatus;
injecting a dialkyl carbonate

 formula (1)

or alkyl aryl carbonate compound of

 formula (2)

and an aromatic hydroxyl compound of formula ArOH, wherein R is alkyl group, and each Ar is an aromatic group having 5 to 30 carbon atoms, into the loop-type reaction apparatus to provide a mixed reaction solution;
filtering the mixed reaction solution to provide a filtered solution which is free of the heterogeneous catalyst;
heating the filtered solution to a desired reaction temperature;
separating high boiling point components and low boiling point components;
outputting the low boiling point components in a gaseous form;
directing the high boiling point components back to the loop-type reaction apparatus; and
outputting the high boiling point components comprising the aromatic carbonate compound.

2. The continuous method for the preparation of the aromatic carbonate of claim 1, wherein said heterogeneous catalyst is a supported catalyst wherein a transition metal oxide is supported on a carrier having a size of 1 to 20 mm.

3. The continuous method for the preparation of the aromatic carbonate of claim 2, wherein said transition metal oxide is selected from the group consisting of $MoO_3$, $Ga_2O_3$, $V_2O_5$, PbO, $ZrO_2$, $TiO_2$, CdO, $Fe_2O_3$, CuO, MgO, $Y_2O_3$, $Mn_3NiO$, ZnO, $Nd_2O_3$, $Co_2O_3$, $RuO_2$, $Nb_2O_5$, $Cr_2O_3$, and a mixture thereof.

4. According to the continuous method of claim 1, wherein the reaction apparatus for the preparation of an aromatic carbonate, comprising
a) a reactor equipped with a filter, which is located inside the reactor, for preventing the output of a heterogeneous catalyst and only outputting reaction solution;
b) a reaction solution circulation pump that is connected to the side of the reactor on which the filter is equipped;
c) a heat exchanger, which is connected between the reaction solution circulation pump and the reactor, for raising the temperature of the reaction solution that is supplied from the reaction solution circulation pump to a desired reaction temperature and evaporating it; and
d) a distillation column, which is connected to the upper portion of the reactor, for separating the evaporated reactants that are generated in the reactor and the heat exchanger into high boiling point components and low boiling point components and then condensing the high boiling point components to withdraw and direct them to the reactor and outputting the low boiling point components in a gaseous form.

5. According to the continuous method of claim 4, wherein the reaction apparatus for the preparation of the aromatic carbonate of, further comprising e) a heat exchanger for cooling, which is connected to the upper portion of the distillation column, for condensing the low boiling point components that are supplied from the distillation column in a gaseous form.

* * * * *